US006171241B1

(12) United States Patent
McVeigh et al.

(10) Patent No.: US 6,171,241 B1
(45) Date of Patent: Jan. 9, 2001

(54) METHOD FOR MEASURING MYOCARDIAL MOTION AND THE LIKE

(75) Inventors: Elliot R. McVeigh, Timonium; Bradley D. Bolster, Jr., Laurel, both of MD (US)

(73) Assignee: The Johns Hopkins University School of Medicine, Baltimore, MD (US)

(*) Notice: Under 35 U.S.C. 154(b), the term of this patent shall be extended for 0 days.

(21) Appl. No.: 09/095,910

(22) Filed: Jun. 11, 1998

Related U.S. Application Data

(60) Provisional application No. 60/049,442, filed on Jun. 12, 1997.

(51) Int. Cl.$^7$ .................................................. A61B 5/055
(52) U.S. Cl. .......................... 600/410; 324/309; 382/128
(58) Field of Search .................................. 600/410, 413; 324/307, 309; 382/128, 107; 128/922

(56) References Cited

U.S. PATENT DOCUMENTS

| | | |
|---|---|---|
| 4,953,554 | 9/1990 | Zerhouni et al. . |
| 5,111,820 | 5/1992 | Axel et al. . |
| 5,195,525 | 3/1993 | Pelc . |
| 5,217,016 | 6/1993 | Axel et al. . |
| 5,275,163 | 1/1994 | McKinnon et al. . |
| 5,281,914 | 1/1994 | Conturo et al. . |
| 5,315,248 | 5/1994 | Yamaguchi . |
| 5,352,979 | 10/1994 | Conturo . |
| 5,379,766 | 1/1995 | McKinnon et al. . |
| 5,512,825 | 4/1996 | Atalar et al. . |
| 5,545,993 | 8/1996 | Taguchi et al. . |
| 5,923,770 * | 7/1999 | O'Donnell et al. ................ 382/131 |
| 6,031,374 * | 2/2000 | Epstein et al. ..................... 324/306 |
| 6,088,472 * | 7/2000 | O'Donnell et al. ................ 382/128 |

OTHER PUBLICATIONS

D.L. Powers, *Boundary valve Problems*, Chapter 1, Fourier Series and Integrals, 1979, pp. 30–42, Academic Press, Inc., Orlando, USA.

E.A. Zerhouni, M.D. Et Al., *Human Heart: Tagging with MR Imaging—A Method for Noninvasive Assessment of Myocardial Motion*, 1988, vol. 169, pp. 59–63, Radiology, USA.

L. Axel, PH.D., M.D. and Lawrence Dougherty, BS, *MR Imaging of Motion With Spatial Modulation of Magnetization*, 1989, vol. 171, pp. 841–845, Radiology, USA.

L. Axel PH.D., M.D. and Lawrence Dougherty, BS, *Heart Wall Motion: Improved Method of Spatial Modulation of Magnetization for MR Imaging*, 1989, vol. 172, pp. 349–350, Radiology, USA.

J. Pauly Et Al., *A k–Space Analysis of Small–Tip–Angle Excitation*, 1989, vol. 81, pp. 43–56, Journal of Magnetic Resonance, USA.

(List continued on next page.)

\* cited by examiner

Primary Examiner—Brian L. Casler
(74) Attorney, Agent, or Firm—Arnold B. Silverman; Eckert Seamans Cherin & Mellott, LLC (57) ABSTRACT

A method of magnetic resonance imaging of myocardial motion includes positioning a portion of a patient such as a patient's heart within a main magnetic field and employing a plurality of RF signals to establish a plurality of parallel plane tags through the portion. In imaging heart motion, a first minimum spacing between adjacent tags is employed in a region where the tags will decrease their separation over systole and a second initial tag separation will be employed for portions wherein the tags increase their separation over systole. The method facilitates simultaneous imaging of both such motions. Fourier coefficients may be employed in establishing the generally parallel tags which may be positioned generally symmetrically about a central tag.

21 Claims, 5 Drawing Sheets

OTHER PUBLICATIONS

T.J. Mosher and Michael B. Smith, *A Dante Tagging Sequence for the Evaluation of Translational Sample Motion,* 1990, vol. 15, pp. 334–339, Magnetic Resonance in Medicine, USA.

E.R. McVeigh, PH.D. and E.A. Zerhouni, M.D., *Noninvasive Measurement of Transmural Gradients in Myocardial Strain with MR Imaging,* 1991, vol. 180, pp. 677–683, Radiology, USA.

E.R. McVeigh and E. Atalar, *Cardiac Tagging With Breath–Hold Cine MRI,* 1992, vol. 28, pp. 318–327, Magnetic Resonance in Medicine, USA.

A.A. Young, PH.D. Et Al., *Validation of Tagging with MR Imaging to Estimate Material Deformation,* 1993, vol. 188, pp. 101–108, Cardiac Radiology, USA.

E.R. McVeigh and Luomin Gao, *Precision of Tag Position Estimation in Breath–hold CINE MRI: The Effect of Tag Spacing,* 1993, pp. 199, John Hopkins University School of Medicine, Baltimore, MD, USA.

E.R. McVeigh, PH.D. and L. Gao, MS, *Resolution and Signal–to–Noise Radio Requirements for Detection of Transmural Gradients in Myocardial Wall Thickening with MR Tagging,* 1993, vol. 193, p. 199, Radiology, USA.

C.C. Moore, BSE Et Al., *Tagging MR Imaging in a Deforming Phantom: Photographic Validation,* 1994, vol. 190, pp. 765–769, Radiology, USA.

W.G. O'Dell, PH.D. Et Al., *Three–Dimensional Myocardial Deformations: Calculation With Displacement Field Image to Tagged MR Images,* 1995, vol. 195, pp. 829–835, Radiology, USA.

E.R. McVeigh, *MRI of Myocardial Function: Motion Tracking Techniques,* 1996, vol. 14. No. 2, pp. 137–150, Magnetic Resonance Imaging, USA.

FIG. 5b     Pixel Number

VTAG
7mm, 6mm, (4.2mm)

FIG. 6a

7mm tag separation

FIG. 6b 4.2mm tag separation

FIG. 6c

METHOD FOR MEASURING MYOCARDIAL MOTION AND THE LIKE

CROSS-REFERENCED TO RELATED APPLICATION

This application claims the benefit of Provisional Application No. 60/049442 which was filed on Jun. 12, 1997 and which is expressly incorporated herein by reference.

BACKGROUND OF THE INVENTION

1. Field of the Invention

The present invention provides a method for sampling motion of portions of a patient such as portions of the heart which have different movement characteristics and, more specifically, the method is directed toward using magnetic resonance imaging with variable separation tagging.

2. Description of the Prior Art

The advantageous use of magnetic resonance imaging wherein a patient or object is placed within a magnetic field with alternating generation of RF pulses and gradient pulses serving to excite nuclei within the area of interest and cause responsive emission of magnetic energy which is picked up by a receiver and may be processed by computer means followed by recording, display or production of hard copy of the results has long been known. See, generally, Atalar-McVeigh U.S. Pat. No. 5,512,825 and Conturo-Robinson U.S. Pat. No. 5,281,914, both of which are assigned to the owner of the present invention, the disclosures of which is expressly incorporated herein by reference.

It has been known to employ two sets of tagging planes oriented orthogonal to the image plane in imaging two dimensional heart wall motion with magnetic resonance imaging through spatial modulation of magnetization (SPAMM) approaches. See U.S. Pat. Nos. 5,111,820 and 5,217,016.

U.S. Pat. No. 5,275,163 discloses the use of magnetic resonance imaging and monitoring motion of a part of an object. Pulse and gradient sequences are applied in pairs with spatially differing tagging patterns with subtraction being employed to form a tagged image.

U.S. Pat. No. 5,352,979 discloses observing a phase angle response of volume elements in a slice or volume and imaging occurring before and during perturbations caused by external stimuli.

U.S. Pat. No. 5,379,766 discloses quantitative motion evaluation of a portion of an object by employing a high contrast tagging grid for detection of tagging patterns.

U.S. Pat. Nos. 5,315,248 and 5,545,993 disclose tracking of motion.

In spite of the foregoing contributions to the art, there remains a need for a method of providing high resolution images of myocardial motion wherein portions of the myocardium being imaged may have different movement characteristics.

SUMMARY OF THE INVENTION

The above-described need has been met by the present invention by providing a means for employing specific RF signals which establish a plurality of tag surfaces which pass through the myocardium and have variable spacing with respect to certain other tag surfaces.

In one embodiment, the imaging of regions of the myocardium wherein the tags will increase their separation over systole, will have tag planes which are placed relatively close together at end-diastole. In regions where the tags decrease their separation over systole, the tags are placed farther apart so they remain detectable at end-systole. For example, the first approach may be taken in connection with radial thickening and the second approach in connection with circumferential shortening.

Both of these types of measurements may be obtained simultaneously with the method of the present invention.

It is an object of the present invention to provide a magnetic resonance imaging method which through the use of variable separation tagging permits obtaining higher resolution sampling of the motion of a material or object.

It is another object of the present invention to provide such high resolution sampling of motion in connection with imaging myocardial motion.

It is a further object of the present invention to provide such a method wherein the customized spacing between tags will be based upon whether the tags increase or decrease their separation over systole during movements.

It is a further object of the present invention to provide such a method which can provide high resolution estimates of radial thickening and circumferential shortening of the myocardium simultaneously.

It is yet another object of the invention to provide such images through variable separation tagging which maintains detectability at end systole.

These and other objects of the invention will be more fully understood from the following description of the invention on reference to the illustrations appended hereto.

DESCRIPTION OF THE PREFERRED EMBODIMENTS

As employed herein the term "patient" means a living member of the animal kingdom including humans.

The prime focus of the method of the present invention is to measure through magnetic resonance imaging moving portions of the myocardium of a patient. The present invention with its variable spacing between tags and specific selection of spacing facilitates such simultaneous imaging of portions of the myocardium which have different motion fields. For example, high resolution sampling of motion of the radial thickening and circumferential shortening responsive to myocardial movement is facilitated.

Figure 1:
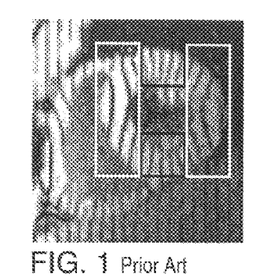
FIG. 1 illustrates a prior art image wherein two modes of strain are sampled with a parallel plane tagging pattern. In the regions outlined with the black squares the tag planes are pushed together by circumferential shortening of the myocardium, in the regions outlined with the white rectangles the tags are stretched farther apart by radial thickening.
Figure 2A:
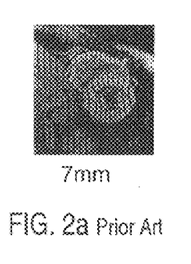
FIGS. 2(a)–2(e) illustrates a prior art approach to myocardial motion imaging with end systolic tagged MR images with different tag separations. The initial separation of the tag planes is given below each image. All tags remain visible until a tag separation of 5 mm. At a 5 mm separation the tags on the free-wall are blurred together, eliminating the possibility of tracking these points.
Figure 2B:
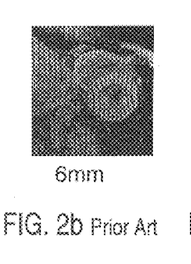
Figure 2C:
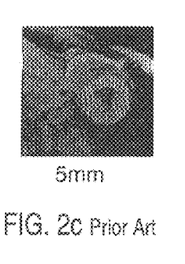
Figure 2D:
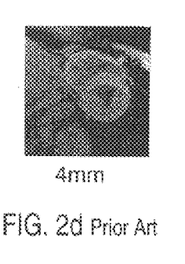
Figure 2E:
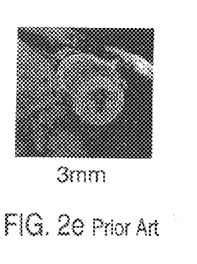

Myocardial tagging with breath-hold imaging has been shown to be an effective method of accurately measuring myocardial motion. See Zerhouni et al., Human Heart: Tagging With MR Imaging—A Method for Noninvasive Assessment of Myocardial Motion, Radiology 169(1):59–63 (1988); Axel et al., MR Imaging of Motion With Spatial Modulation of Magnetization, Radiology 171(3):841–845 (1989); McVeigh et al., Cardiac Tagging With Breath-Hold Cine MRI, Magn. Reson. Med. 28(2):318–327 (1992); O'Dell et al., Displacement Field Fitting for Calculating 3D Myocardial Deformations From Tagged MR Images, Radiology 195:829–835 (1995); Young et al., Validation of Tagging With MR Imaging to Estimate Material Deformation, Radiology 188:101–108 (1993); and Moore et al., Tagged MR Imaging in a Deforming Phantom—Photographic Validation, Radiology 190:765–769 (1994). The spatial resolution of motion estimates is limited by the achievable density of tag points in the myocardium. Parallel plane tagging patterns are easy to generate and detect, and the Fourier coefficients of this tagging pattern are compacted along the readout axis permitting fast sampling for low motion blurring. See Axel et al., MR Imaging of Motion With Spatial Modulation of Magnetization, Radiology 171 (3):841–845 (1989); McVeigh et al., Cardiac Tagging With, Breath-Hold Cine MRI, Magn Reson Med 28(2):318–327 (1992); Mosher et al., A DANTE Tagging Sequence for the Evaluation of Translational Sample Motion, Magn Reson Med 15(2):334–339 (1990); and McVeigh, E. R., MRI of Myocardial Function: Motion Tracking Techniques, Magn. Reson. Imag. 14(2): 137–150 (1996). The parallel plane tagging pattern, however, as well as the grid pattern, results in non-optimal sampling of the cardiac motion as shown in FIG. 1. There is a significant decrease in tag separation during systole in the regions sampling circumferential shortening, while regions sampling radial thickening show an increase in tag separation. To increase the density of tag point samples in the radial direction, tag planes can be moved closer together. Unfortunately, it has been shown that a distance of approximately 3–4 pixels or 4–6 mm between tag planes is required to resolve the location of the tags consistently although this depends on slice thickness. See McVeigh et al., Precision of Tag Position Estimation in Breath-Hold CINE MRI: The Effect of Tag Spacing, Society of Magnetic Resonance in Medicine, Book of Abstracts (1):199 (1993) and McVeigh et al., Resolution and SNR Requirements for Detecting Transmural Gradients in Myocardial Wall Thickening With MR Tagging, Radiology 193 (P):199 (1994). As the slice becomes thinner, the intrinsic signal to noise ratio is reduced, therefore tag detection is more difficult; however, with thinner slices through-plane shears cause less tag blurring. We have found that the initial separation of the tag planes should be chosen so that the tags sampling circumferential shortening remain at least about 3–4 pixels or 4–6 mm apart at end-systole, setting the limit on the minimum tag separation. However, the separation of the tags sampling radial thickening can begin at about 3–4 pixels or 4–6 mm apart, because they will spread farther apart during contraction.

A demonstration of this tag density problem is shown in FIGS. 2(a)–2(e). Here, the same heart is tagged with parallel plane tags of different uniform separations. If the initial tag plane separation is too small, the tags that are sampling circumferential shortening blur into a uniform gray signal by the end of systole, and all tracking information is lost. When the initial tag separation is less than 4 mm or 3 pixels in FIG. 2, the tags completely disappear in the regions at 12 and 6 o'clock. However, it is also clear from this picture that the radial thickening is sampled very well, in fact, for the 4 mm or 3 pixel initial tag separation there are three independent tag position estimates across the wall. With uniform tag plane separations, one must sacrifice this high density sampling of radial thickening to maintain an adequate tag separation for sampling the circumferential shortening. The present invention provides a method for producing a variable separation tagging pattern to obtain a higher density of motion estimates than obtained with a uniform tag plane separation.

Figure 3:
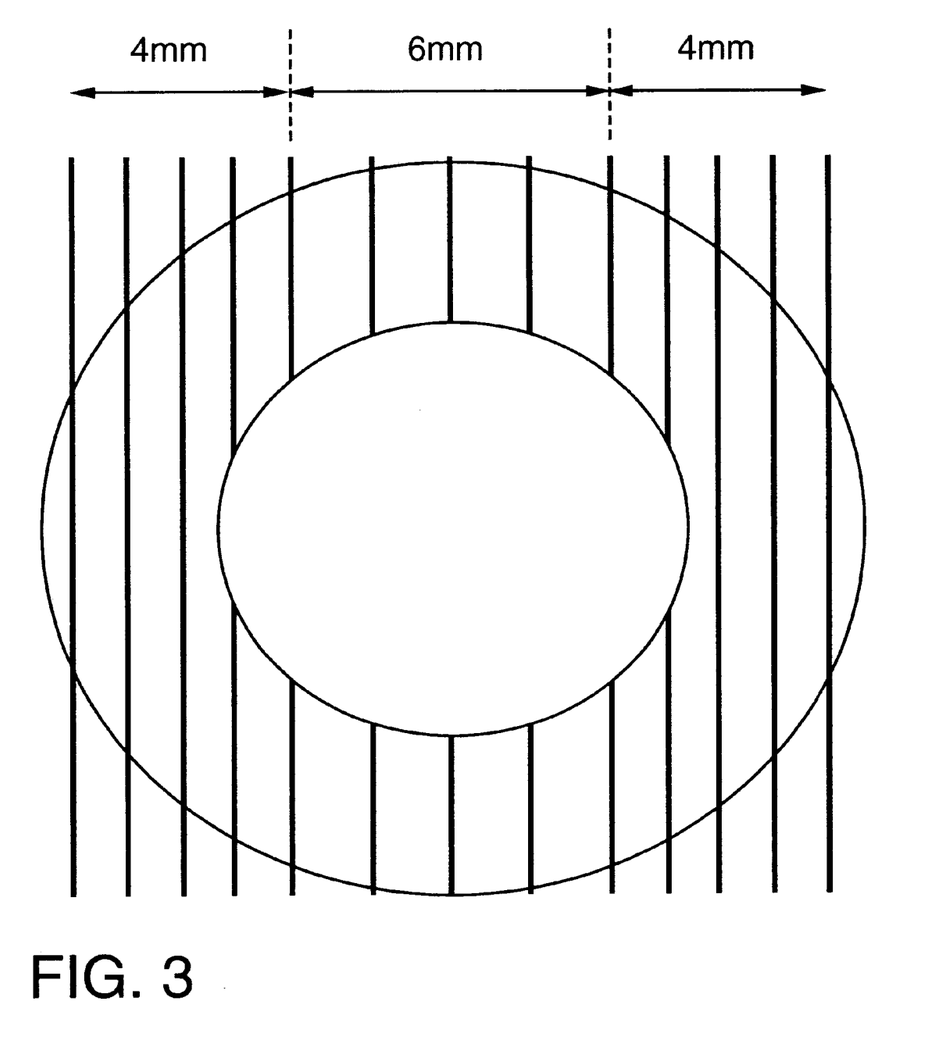
FIG. 3 illustrates schematically a variable separation tagging pattern of the present invention in which 13 tag lines are placed across the left ventricle. Two tag separations are used in this particular pattern; a region sampling circumferential shortening with 6 mm separations, and two regions sampling radial thickening with 4 mm initial separations. The pattern is easily adjusted to the dimensions of a particular heart.

In order to match the left ventricular short axis displacement field, a variable separation tagging pattern can be used. If the initial tag separation is set in the region sampling circumferential shortening to approximately 6 pixels, and the initial tag separation in the region sampling radial thickening to approximately 4 pixels or 6 mm, radial thickening will be sampled with higher density without losing tag information in the circumferential shortening direction. Therefore, both strains will be measured more accurately than with parallel tags of equal separation. For a human heart, if it is assumed, for example, that 13–15 tags are desired across the left ventricle, these tags can be placed on either side of the central column of the image, with separations on each side as follows: 6 mm, 6 mm, 4 mm, 4 mm . . . . In most hearts, this will yield two tags across the heart wall in the region sampling radial thickening, as shown in FIG. 3. In the form shown in FIG. 3, the tag to adjacent tag spacing is symmetrical about the center tag and is greatest in the central region. It is advantageous to use a parallel plane tagging geometry to keep the Fourier coefficients of the tagging pattern concentrated along the readout axis, as previously mentioned. See McVeigh, E. R. MRI of Myocardial Function: Motion Tracking Techniques, Magn. Reson. Imag. 14(2):137–150 (1996).

A simple method for achieving a variable separation tag pattern is to explicitly define the location of the tags with a multi-spectral radio-frequency (RF) pulse. See McVeigh et al., Noninvasive Measurement of Transmural Gradients in Myocardial Strain With Magnetic Resonance Imaging, Radiology 180(3):677–683 (1991). This tagging pattern could be created by applying a constant gradient in the readout direction which is normal to the tag direction and playing an RF pulse that is the summation of phase modulated waveforms at the appropriate frequency offsets. One disadvantage of explicitly defining the location of each tag plane is the relatively high RF power requirements, resulting in a prohibitively long pulse. This problem may be circumvented by designing the tagging pulse as a sequence of non-selective RF pulses separated by a short gradient pulse or blip. During the RF pulses the gradient is off, which contracts the sample bandwidth, thus reducing the power requirements.

The sequence of RF pulses can be designed for the variable spaced tagging pattern using concepts from k-space excitation theory (Pauly et al., A k-Space Analysis of Small-Tip-Angle Excitation, J Magn Reson 81:43–56 (1989)). First, one generates the Fourier coefficients of the variable spaced tag pattern, then one uses those coefficients to construct an RF pulse train. Suppose the desired tagging pattern is f(x)*g(x), where g(x) is the tag profile and f(x) is a symmetric distribution of impulses such as that shown in FIG. 3.

$$f(x) = \delta(x) + \sum_{j=1}^{J} (\delta(x - x_j) + \delta(x + x_j)) \tag{1}$$

Here δ(x) is the central tag position with J tags on either side of the center. Because a finite number of RF pulses are used in the tag generation pulse, the tag pattern will be periodic. The function in Equation 1 is non-periodic, so it has a continuous Fourier spectrum, however, its periodic extension can be represented by a discrete Fourier series. See Powers, D. L., Boundary Value Problems, Academic Press, Inc. Orlando. 30–42.1979. If the width of the desired pattern f(x) is 2L, the periodic extension can be written $$\tilde{f}(x+m2L) = \tilde{f}(x), m = \pm 1, \pm 2, \ldots \tag{2}$$

where $-L < x \leq L$. The resulting Fourier series coefficients for $\tilde{f}(x)$ are:

$$a_0 = \frac{1}{2L}(2J+1) \tag{3}$$

$$a_n = \frac{1}{L}\left(1 + 2\sum_{j=1}^{J} \cos\left(\frac{n\pi x_j}{L}\right)\right), n = 1, \ldots, \infty$$

where $a_0$ is the amplitude of the first RF pulse, $x_j$ is the position of an individual tag with respect to the center of the tagging pattern, and L is the length of one side of the symmetric tagging pattern. The Fourier series for $\tilde{f}(x)$ can be written:

$$\tilde{f}(x) = a_0 + \sum_{n=1}^{\infty} a_n \cos\left(\frac{n\pi x}{L}\right). \tag{4}$$

The sine terms do not appear because $\tilde{f}(x)$ is an even function. The coefficients $a_n$ are the relative amplitudes used in the RF pulse train. The periodic extension of the tagging pattern into regions of the field of view outside the heart does not have a detrimental effect on the measurement of myocardial motion.

Figure 4A:
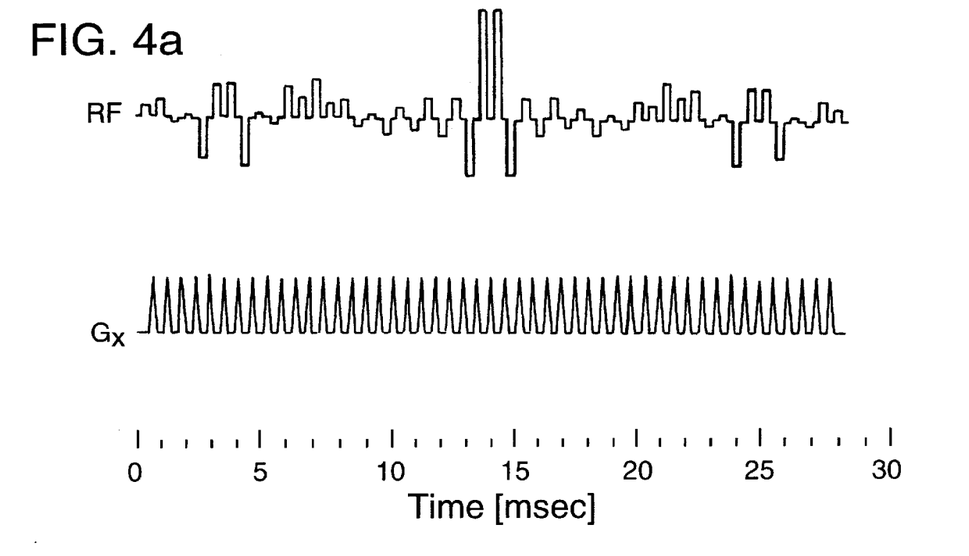
FIG. 4(a) illustrates a variable tag pulse sequence of the present invention with 50 RF pulses which generates separations of 6, 6, 4, 4, 4, 4, 4, 4 mm.
Figure 4B:
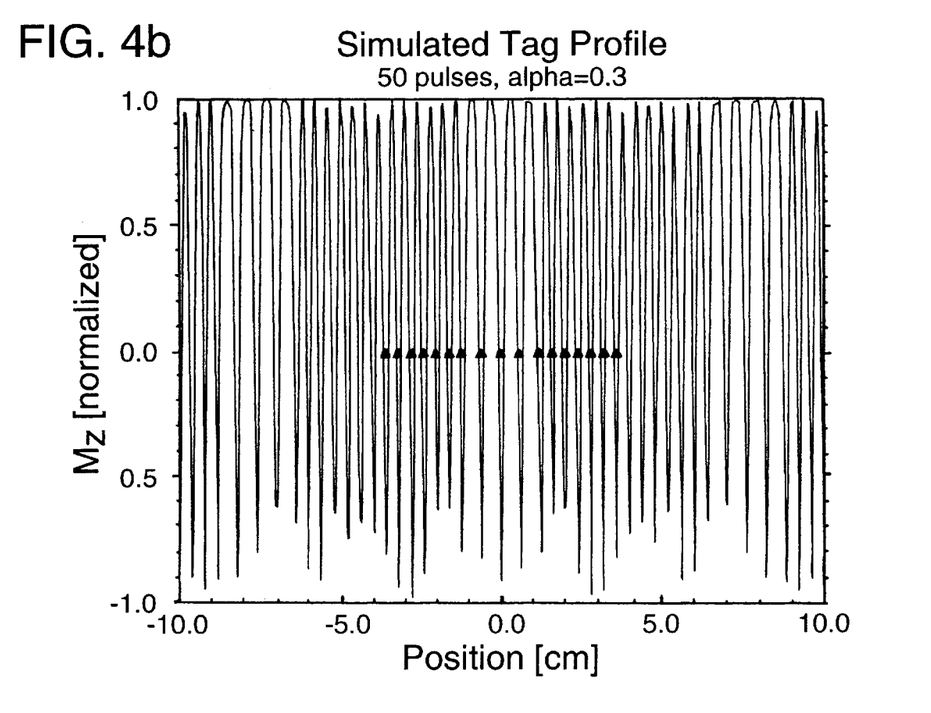
FIG. 4(b) is a Bloch simulation output of $M_Z(x)$, for the sequence shown in FIG. 4(a). The solid triangles denote the desired tag positions input by the user.

An example RF pulse train for producing variable separation tagging is shown in FIG. 4(a). The algorithm to generate the RF amplitudes in the pulse train was the following: the explicit tag positions, $x_j$, were input by the user, and the Fourier series coefficients were calculated using Equation 3. The first 25 coefficients were selected as the RF pulse amplitudes and the pulse train was created by symmetrically repeating the 25 pulses about the center of the pulse train, effectively doubling the applied power. A Hanning window with an alpha of 0.3 was applied to the resulting waveform to reduce RF truncation artifacts in the tagging pattern. Excitation k-space is traversed by playing a gradient "blip," i.e., a short gradient pulse, between each hard RF pulse. After the tagging sequence, all transverse magnetization is spoiled. As with SPAMM (Axel et al., Heart Wall Motion: Improved Method of Spatial Modulation of Magnetization for MR Imaging, Radiology 172(2) :349–360; 1989) and DANTE (Mosher et al., A DANTE Tagging Sequence for the Evaluation of Translational Sample Motion, Magn Reson Med 15(2):334–339; 1990), the gradient direction is normal to the tag planes. Bloch equation simulations were used to calculate the tagging pattern $M_z(x)$ produced by the pulse sequence in FIG. 4(a). This is shown in FIG. 4(b).

Figure 5A:
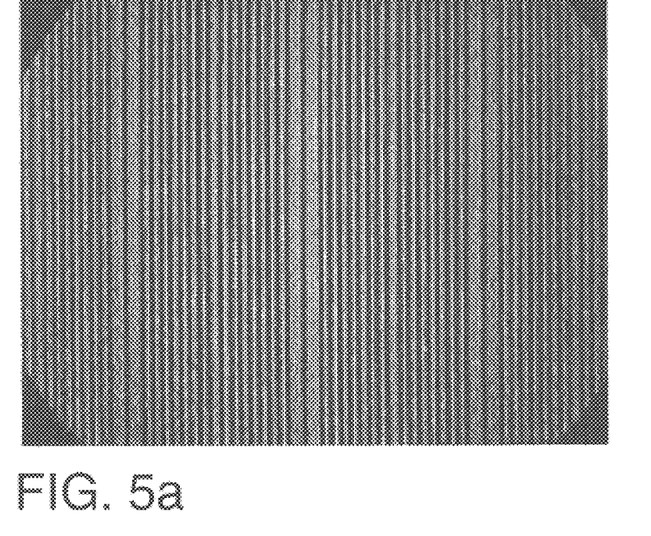
FIG. 5(a) illustrates an image in phantom of the variable spacing tag pattern of the present invention with separations set to 7, 4, 4, 4, 4, 4, 4, 4 mm.
Figure 5B:
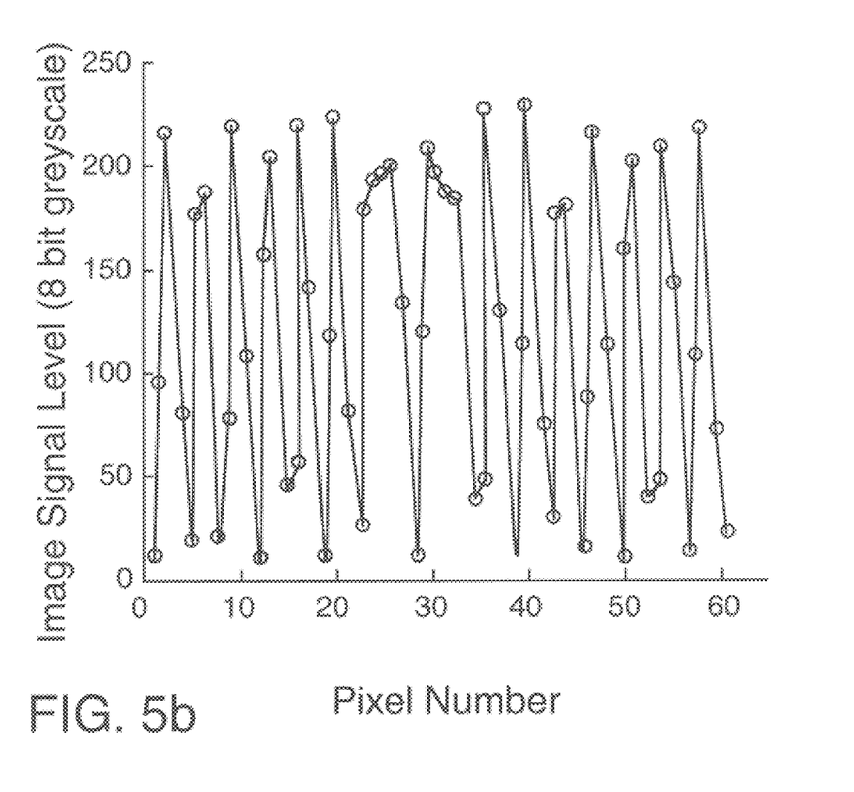
FIG. 5(b) illustrates a profile through the center of the phantom showing tag profiles and tag separation. The circles are the individual pixel values.
Figure 6A:
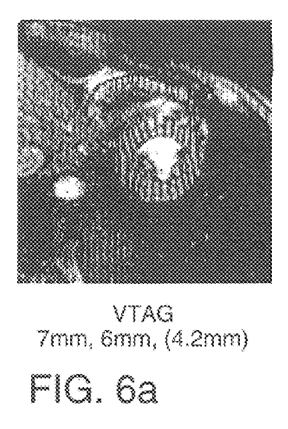
FIG. 6(a) is a variable spaced tag image of the present invention.
Figure 6B:
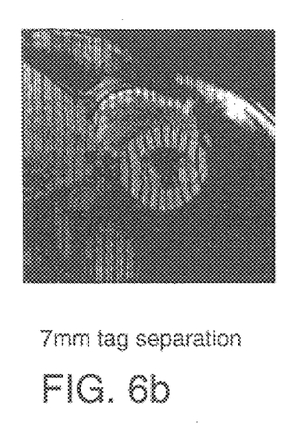
FIGS. 6(b) and (c) illustrate fixed identical tag spacing of the prior art. A comparison of a variable separation tagging image, with two standard parallel tagged images.
Figure 6C:
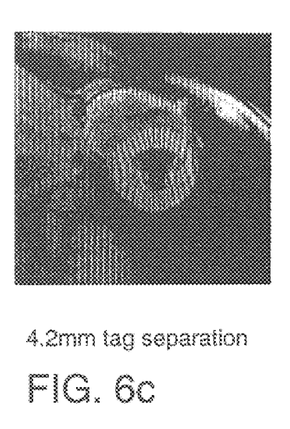

FIG. 5(a) shows the pattern in a phantom using 40 pulses. FIG. 5(b) shows an associated profile through this image. These tags are of comparable quality to those generated with constant tag separation. FIGS. 6(a)–(c) shows a comparison of the variable separation tagging pattern with standard parallel tags in the same heart shown in FIGS. 2(a)–(e). The variable separation tagging pulse train was 28 ms and created a pattern with a 5 pixel tag separation between the center tag and its closest neighbors, 4.3 pixel separation for the next tag, and a 3 pixel separation for the remaining tags. Compared with a constant tag separation of 5 pixels, 6 additional tags are obtained across the heart at the mid short axis plane using the variable separation tagging pattern. The standard image with 5 pixel tag separation does not sample the radial thickening with high spatial resolution. The standard image with 3 pixel tag separation does not resolve the individual tags in the circumferential shortening region. With the variable separation tagging pattern, both of these regions are sampled well, and the tags remain visible throughout systole. The blood as shown in FIG. 6(a) is white and the blood in FIGS. 6(b) and 6(c) has been saturated and, therefore, is black.

The method of the present invention facilitates simultaneous sampling of circumferential shortening and radial thickening with the appropriate spatial resolution using variable separation tag planes. An alternate approach to increasing the spatial resolution of the tagging pattern is to interleave two acquisitions with the tagging pattern shifted by ½ tag separation on the second acquisition. There are two problems with this approach: the imaging time is increased by a factor of two, and the shifted acquisitions must occur in the same breath-hold to ensure an even sampling. A better use of the time required for the "second" acquisition in the same breath-hold is to obtain the orthogonal displacement information by rotating both the tagging pattern and the readout gradient 90 degrees. See McVeigh et al., Cardiac Tagging With Breath-Hold Cine MRI, Magn Reson Med 28(2):318–327 (1992) and McVeigh, E. R., MRI of Myocardial Function: Motion Tracking Techniques, Magn. Reson. Imag. 14(2):137–150 (1996).

Quantitative MR cardiac stress testing with tagging requires very rapid data acquisition due to the limitations on the total time of dobutamine infusion. For each dobutamine infusion rate (stress level), the tagging data should be obtained within 3–4 minutes. Therefore, variable separation taggings will be preferable to shifted tags under these time constraints. In addition, the flexibility of the variable separation tagging sequence makes it tunable to the dobutamine stressed heart in which myocardial shortening becomes enhanced and the disparity between circumferential shortening and radial thickening becomes greater.

The 20–30 ms time involved in generating variable separation taggings in their present form is longer than that required for generating a constant separation tagging pattern. FIG. 4(a) shows several RF pulses that have very low or even zero amplitude. The length of the variable separation tagging pulse train could be reduced in length by removing the low amplitude pulses and combining adjacent gradient pulses into a single pulse. This is equivalent to choosing only terms in Equation 3 that make a significant contribution to the tag pattern function f(x). In addition, the sequence is presently implemented on a "standard" gradient system with a maximum gradient slew rate of 16.7 T/m/sec. Once this sequence is implemented on the enhanced gradient system with 170 T/m/sec slew rate, the 28 ms variable separation tagging pulse shown in FIG. 4. can be performed in 16.3 ms. The combination of a reduction in the number of RF pulses and increased slew rate should bring this sequence below 10 ms making it comparable to the uniform separation tagging sequences presently used.

The variable separation parallel plane tagging of the present invention provides high resolution images of myocardial motion. It also provides high resolution measurements of radial thickening and circumferential shortening simultaneously.

While for simplicity of disclosure specific reference has been made herein to heart movement, such as myocardial motion, the invention is not so limited. The invention may be employed in the measurement of inhomogeneous motion fields. The variable spacing of the MR tagging pattern can readily be adjusted as needed on a tag-to-tag basis. The invention may be employed readily, for example, on blood vessels, organs and muscles other than the myocardium.

Whereas particular embodiments of the invention have been described herein for purposes of illustration, it will be evident to those skilled in the art that numerous variations of the details may be made without departing from the invention as defined in the appended claims.

What is claimed is:

1. A method of magnetic resonance imaging motion of a portion of a patient comprising positioning a patient's heart within a main magnetic field, employing a plurality of RF pulses to establish a plurality of parallel plane tags through said portion, employing a first spacing between adjacent said tags in a first region, establishing a second minimum spacing between adjacent said tags in a second region, and said first spacing being different from said second minimum spacing.

2. The method of claim 1 including employing said method in measuring myocardial motion.

3. The method of claim 2 including establishing said plurality of parallel plane tags through the myocardium.

4. The method of claim 3 including employing said first spacing in said first region where said tags decrease their separation over systole, and employing said second minimum spacing in said second region where said tags increase their separation over systole.

5. The method of claim 4 including employing said method where said first minimum spacing is employed in connection with imaging circumferential shortening, and employing said second minimum spacing in a region sampling radial thickening of said myocardium.

6. The method of claim 5 including effecting said imaging of said circumferential shortening and said radial thickening substantially simultaneously.

7. The method of claim 6 including said first spacing being of greater magnitude than said second minimum spacing.

8. The method of claim 7 including establishing said plurality of parallel plane tags with generally symmetrical spacing about a central said tag.

9. The method of claim 6 including employing at least two tag separation sizes in said first spacing.

10. The method of claim 9 including employing at least two tag separation sizes in said second minimum spacing.

11. The method of claim 10 including employing separations of about 4 to 6 mm in said second minimum spacing.

12. The method of claim 9 including employing separations of about 4 to 6 mm in said first spacing.

13. The method of claim 1 including employing a multi-spectral radio-frequency pulse as said RF pulse.

14. The method of claim 13 including providing a constant gradient pulse during said RF pulse applied generally normal to said tag planes.

15. The method of claim 1 including creating said tag spacing by generating Fourier coefficients of the variable spaced tag planes and employing said coefficients to construct said RF pulses.

16. The method of claim 15 including employing as said Fourier coefficients, coefficients determined by the following equations:

$$a_0 = \frac{1}{2L}(2J+1)$$

$$a_n = \frac{1}{L}\left(1 + 2\sum_{j=1}^{J}\cos\left(\frac{n\pi x_j}{L}\right)\right), n = 1, \ldots, N$$

wherein $a_0$ represents the amplitude of the first RF pulse, $a_n$ represents the amplitude of the RF pulse train and "$n$" indicates the number of a given pulse, $x_j$ is the position of an individual tag with respect to the center of the tagging pattern, J represents the individual tags on either side of the center tag, L is the length of one side of the tagging pattern, and N+1 is the total number of pulses.

17. The method of claim 16 including establishing a symmetric distribution of RF pulses in accordance with the relationship of claim 15 wherein $$\frac{-N}{2} \leq n \leq \frac{N}{2},$$

18. The method of claim 1 including employing as said first spacing about 4 to 6 mm, and effecting smaller spacing between at least some adjacent parallel tags of said tags having said second minimum spacing.

19. The method of claim 18 including said tags being spaced symmetrically about a central tag.

20. The method of claim 1 including employing a train of non-selective RF pulses as said RF pulses.

21. The method of claim 20 including providing gradient pulses separating said non-selective components of said RF pulses.

* * * * *

UNITED STATES PATENT AND TRADEMARK OFFICE
CERTIFICATE OF CORRECTION

PATENT NO. : 6,171,241 B1
DATED : January 9, 2001
INVENTOR(S) : Elliot R. McVeigh et al.

It is certified that error appears in the above-identified patent and that said Letters Patent is hereby corrected as shown below:

Title page,
OTHER PUBLICATIONS, D.L. Power, "*valve*", should be -- *value* --.

Column 7,
Lines 35, "employing" should be -- applying --.
Line 37, 50, 52, 56 and 60, "employing" should be -- establishing --.
Line 40, "and" should be -- wherein --.
Line 41, "being" should be -- is --.
Line 44, should read: -- The method of claim 1 including the step of --.
Line 45, "employing said method in" should be deleted.
Line 56, "said method where" should be deleted.
Line 57, "is employed" should be deleted.
Line 63, "effecting said" should be deleted.

Column 8,
Lines 8, 11, 15, 25, 28 and 54, "employing" should be -- establishing --.
Lines 18 and 61, "employing" should be -- applying --.
Line 28, "coefficients.coefficients" should read -- coefficients are --.
Line 54, "spacing about" should read -- spacing to about --.
Line 59, "being spaced" should be -- spacing --

Signed and Sealed this

Twenty-eighth Day of May, 2002

*Attest:*

JAMES E. ROGAN
*Attesting Officer*    *Director of the United States Patent and Trademark Office*

UNITED STATES PATENT AND TRADEMARK OFFICE
CERTIFICATE OF CORRECTION

PATENT NO.      : 6,171,241 B1
DATED           : January 9, 2001
INVENTOR(S)     : Elliot R. McVeigh et al.

It is certified that error appears in the above-identified patent and that said Letters Patent is hereby corrected as shown below:

<u>Column 1,</u>
Line 4, after the title, the following should be inserted:

-- <u>Statement of Government Interest</u>

This invention was made with support from the Departments of Biomedical Engineering and Radiology, NIH grants HL45683 and HL45090. --

Signed and Sealed this

Fourteenth Day of October, 2003

JAMES E. ROGAN
*Director of the United States Patent and Trademark Office*